United States Patent
Oster (10) Patent No.: US 8,772,522 B2
(45) Date of Patent: Jul. 8, 2014

(54) SALTS OF 5-SULFOISOPHTHALIC ACID AND METHOD OF MAKING SAME

(75) Inventor: Timothy A. Oster, Batesville, AR (US)

(73) Assignee: Futurefuel Chemical Company, Clayton, MO (US)

( * ) Notice: Subject to any disclaimer, the term of this patent is extended or adjusted under 35 U.S.C. 154(b) by 24 days.

(21) Appl. No.: 13/586,024

(22) Filed: Aug. 15, 2012

(65) Prior Publication Data

US 2013/0211116 A1 Aug. 15, 2013

Related U.S. Application Data

(60) Provisional application No. 61/632,835, filed on Aug. 16, 2011.

(51) Int. Cl.
*C07F 5/00* (2006.01)
*C07F 7/00* (2006.01)
*C07F 13/00* (2006.01)
*C07F 15/00* (2006.01)

(52) U.S. Cl.
USPC .......... 556/45; 556/1; 556/54; 556/111; 556/120; 556/139

(58) Field of Classification Search
USPC .......... 556/1, 45, 54, 111, 120, 139
See application file for complete search history.

(56) References Cited

U.S. PATENT DOCUMENTS

2002/0169273 A1* 11/2002 Duan ............. 528/286
2009/0054567 A1* 2/2009 Heater ............. 524/131
2010/0239512 A1* 9/2010 Morris et al. .......... 424/65

FOREIGN PATENT DOCUMENTS

WO WO 2011-049940 A2 * 4/2011

OTHER PUBLICATIONS

International Search Report of PCT/US2012/050909 (2013).*

* cited by examiner

*Primary Examiner* — Porfirio Nazario Gonzalez
(74) *Attorney, Agent, or Firm* — Husch Blackwell LLP (57) ABSTRACT

This invention relates to methods for the production of various metal salts of 5-sulfoisophthalic acid including those where the metal cation is selected from the group consisting of silver (I), sodium, potassium, rubidium, cesium, magnesium, calcium, strontium, barium, manganese (II), iron (II), cobalt (II), nickel (II), copper (I), copper (II), zinc, yttrium, and cadmium. The methods utilize a solvent system that comprises acetic acid or water or a mixture of both. The invention also encompasses the various metal salts of 5-sulfoisophthalic acid.

21 Claims, 1 Drawing Sheet

SALTS OF 5-SULFOISOPHTHALIC ACID AND METHOD OF MAKING SAME

CROSS REFERENCE TO RELATED APPLICATION

This application claims priority from U.S. Provisional Application Ser. No. 61/632,835 filed on Aug. 16, 2011, the entire disclosure of which is incorporated herein by reference.

FIELD OF THE INVENTION

This disclosure relates to the field of production of salts of derivatives of isophthalic acid. In particular, this disclosure relates to the production of metal salts of 5-sulfoisophthalic acid.

BACKGROUND

This disclosure is intended to teach by way of example and not by way of limitation.

This disclosure relates to the field of specialty chemicals. In particular, this disclosure relates to the preparation of salts of 5-sulfoisophthalic acid. More particularly, this disclosure relates to the preparation of various metal (Mt) salts of 5-sulfoisophthalic acid (MtSIPA) from 5-sulfoisophthalic acid (SIPA or HSIPA) via an acetic acid or water or acetic acid/water solvent system using a metal cation producing compound.

Salts of HSIPA, particularly lithium ($Li^+$) and sodium ($Na^+$), are primarily used as additives in the production of polymers. Other salts of HSIPA, or derivatives thereof, are used in a variety of other applications. For example, the silver salt of dimethyl 5-sulfoisophthalate (AgDMSIPA), is used as an antimicrobial additive in polymers. Given that silver is a known antimicrobial agent, it is anticipated that a silver (I) salt of HSIPA will exhibit antimicrobial properties and may also function as a desired additive for certain polymer processes.

Furthermore, it is known in the industry that metal salts of HSIPA (e.g., sodium and lithium) often can be used as substitutes for the same salts of the dimethyl ester of 5-sulfoisophthalate (DMSIPA). The advantages of using 5-sulfoisophthalic acid salts rather than the dimethyl ester salts of 5-sulfoisophthalate include (1) lower cost due to the elimination of a process step (esterification of HSIPA), (2) elimination of the need to vigorously dry the process intermediate (HSIPA) as required during the esterification step of the DMHSIPA process, and (3) elimination of a flammable byproduct (methanol) during the preparation of the MtDMSIPA. Thus there is interest in and a need for developing new salts of 5-sulfoisophthalic acid and for exploring their chemical behaviors and potential uses.

Developing a commercially viable method of manufacture for MtSIPA presents several challenges, one of which is the variability in HSIPA chemistry. HSIPA chemistry is such that one cannot necessarily take a known process for making one salt (e.g., LiSIPA), switch out the metal (e.g., switch to Na), and expect that the process will result in a similar salt product. For example, one can wash a crude NaSIPA product with water but doing the same with LiSIPA results in lost product. Likewise, washing crude LiSIPA with acetic acid results in a hydrate or anhydrous product whereas washing crude NaSIPA with acetic acid results in a solvate. Also, one metal cation may require a different solvent system than another metal cation.

In addition, many of the known processes for producing HSIPA salts results in product having high sulfate levels. A high sulfate HSIPA salt can cause problems in polymer processes. For example, LiSIPA salts with accompanying high levels of sulfate are associated with high levels of nylon filament breakage due to sulfate precipitation. Accordingly, HSIPA salts with a low-sulfate composition are of value because they are expected to cause fewer problems in polymer production processes.

For these and other reasons, there is a need for new HSIPA salts and for a manufacturing process that is commercially feasible, economically efficient and avoids or eliminates some of the major problems that hinder other HSIPA salt production methods (e.g., high sulfate levels).

SUMMARY OF THE INVENTION

There is now a process for the preparation of metal salts of 5-sulfoisophthalic acid (MtSIPA) via the use of an acetic acid, or water, or acetic acid/water solvent system. In broad terms, the process comprises the steps of forming a solvent system comprising 5-sulfoisophthalic acid, a metal cation producing compound, and acetic acid and water wherein the acetic acid to water ratio is between and includes 0:1 to 1:0. The metal cation in the metal cation producing compound is selected from the group consisting of silver (I), sodium, potassium, rubidium, cesium, magnesium, calcium, strontium, barium, manganese (II), iron (II), cobalt (II), nickel (II), copper (I), copper (II), zinc, yttrium, and cadmium. The solvent system is then maintained under conditions sufficient to form a metal salt of 5-sulfoisophthalic acid.

In another aspect, the invention is a process for the preparation of a metal salt of 5-sulfoisophthalic acid where the process comprises the step of contacting previously isolated 5-sulfoisophthalic acid with a metal cation producing compound under conditions sufficient to form a metal salt of 5-sulfoisophthalic acid. The metal cation for the metal cation producing compound is selected from the group consisting of silver (I), sodium, potassium, rubidium, cesium, magnesium, calcium, strontium, barium, manganese (II), iron (II), cobalt (II), nickel (II), copper (I), copper (II), zinc, yttrium, and cadmium.

The metal salts resulting from the process according to the invention are silver (I) SIPA (AgSIPA), sodium SIPA (NaSIPA), potassium SIPA (KSIPA), rubidium SIPA (RbSIPA), cesium SIPA (CsSIPA), magnesium SIPA ($Mg(SIPA)_2$), calcium SIPA ($Ca(SIPA)_2$), strontium SIPA ($Sr(SIPA)_2$), barium SIPA ($Ba(SIPA)_2$), manganese (II) SIPA ($Mn(SIPA)_2$), iron (II) SIPA ($Fe(SIPA)_2$), cobalt (II) SIPA ($Co(SIPA)_2$), nickel (II) SIPA ($Ni(SIPA)_2$), copper (I) SIPA (CuSIPA), copper (II) SIPA ($Cu(SIPA)_2$), zinc SIPA ($Zn(SIPA)_2$), yttrium SIPA ($Y(SIPA)_3$) and cadmium SIPA ($Cd(SIPA)_2$).

The invention also encompasses a composition of matter comprising the reaction product of 5-sulfoisophthalic acid and a metal cation producing compound where the metal cation is selected from the group consisting of silver (I), strontium, iron (II), copper (I), yttrium, and cadmium.

The invention also encompasses various metal salts of 5-sulfoisophthalic acid including the silver (I) salt, the strontium salt, the iron (II) salt, the copper (I) salt, the yttrium salt, and the cadmium salt.

DESCRIPTION OF PREFERRED EMBODIMENT(S)

The term "drowning" as used herein means the addition of one liquid component to another liquid component. In other words, the term means pouring a solution or intermediate slurry into a second liquid.

The claimed invention relates to various metal salts of 5-sulfoisophthalic acid (MtSIPA) and a process of manufacturing these MtSIPA salts. This detailed description begins with a currently preferred process for manufacturing such salts. This exemplary embodiment is provided to aid in the understanding of the invention and should not be interpreted as limiting the scope of the invention.

The claimed process, in a simplified form, comprises the steps of contacting 5-sulfoisophthalic acid: a metal salt; and acetic acid or water or a mixture of the two in a solvent system under conditions sufficient to form a metal salt of 5-sulfoisophthalic acid. The metal salt of 5-sulfoisophthalic acid is then recovered and sold or utilized in other industrial processes. The following will describe the process in more detail.

Although the invention pertains to the manufacture of the MtSIPA, the overall industrial process can begin with the production of 5-sulfoisophthalic acid (HSIPA) and this is where the discussion of this exemplary embodiment begins.

Figure 1:
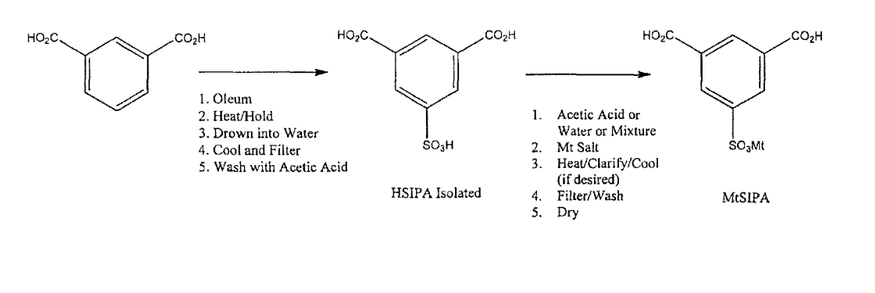
FIG. 1 is a schematic of an exemplary reaction incorporated in the process according to the invention.

Turning now to FIG. 1, isophthalic acid is sulfonated to form HSIPA. There are several known methods for sulfonating isophthalic acid such as combining it with oleum or pure $SO_3$. Any of these known methods of producing HSIPA in an aqueous, dilute sulfuric acid solution are acceptable in the practice of the invention. In this exemplary embodiment isophthalic acid is sulfonated by reacting it with oleum (aka "fuming sulfuric acid") under temperature and time conditions sufficient to form a crude sulfonation solution of HSIPA in sulfuric acid. In a preferred embodiment the oleum is in solution at a concentration between about 20% and 60% and the sulfonation mixture is heated to a temperature between about 150° C. to about 230° C. for a time sufficient to form HSIPA.

The sulfonation solution of HSIPA is drowned into water to generate an aqueous solution that is typically approximately 25% to 40% HSIPA by weight, more preferably around 35% HSIPA, in 20% to 50% sulfuric acid. Those skilled in the art will recognize that the percentages discussed herein can be altered, sometimes significantly, based upon the particular manufacturing equipment and physical constraints in a production facility.

The drowned solution of HSIPA is then cooled to crystallize the HSIPA. The resulting slurry is filtered, washed to remove sulfuric acid and other impurities, and dried to provide HSIPA as a hydrate or as the anhydrous salt depending on the drying conditions. This HSIPA intermediate product is then utilized in the manufacture of the claimed MtSIPA.

As used herein, the term "previously isolated" HSIPA means HSIPA that is isolated or recovered as an intermediate product from a typical sulfonation solution as described above. Broadly speaking it includes HSIPA in any form other than that found in the sulfonation solution or immediately after the typical drowning step. In other words, "previously isolated HSIPA" is meant to include HSIPA that has undergone some minimal step to reduce the sulfate content of the HSIPA product. In most instances it is envisioned that the previously isolated HSIPA used in the practice of the invention is HSIPA that has undergone the typical recovery and washing processes used to make HSIPA that is sold on the open market as an intermediate product for use in other chemical processes.

The previously isolated intermediate HSIPA is contacted with a metal cation producing compound. The term "metal cation producing compound" as used herein includes those metal compounds capable of releasing a cation to react with another anion and more particularly, those metal compounds that form metal cations in solution. Metal cation producing compounds suitable for use in the practice of the invention include standard organic and inorganic metal salts including but not limited to metal hydroxides, metal acetates, metal carbonates, metal oxides, metal halides or a mixture of any of these or other suitable salts. Some metal salts may work better in any given production process and the ultimate choice of salt likely will be based on cost considerations.

Metal salts suitable for use in the practice of the invention include those salts of metal cations selected from the group consisting of silver (I), sodium, potassium, rubidium, cesium, magnesium, calcium, strontium, barium, manganese (II), iron (II), cobalt (II), nickel (II), copper (I), copper (II), zinc, yttrium, and cadmium. Alternative groupings include a process where the metal cation is selected from the group consisting of sodium, potassium, and rubidium; or where the metal cation is cesium; or where the metal cation is selected from the group consisting of magnesium, calcium, and barium; or where the metal cation is selected from the group consisting of manganese (II), cobalt (II), nickel (II), copper (I), and zinc; or where the metal cation is selected from the group consisting of silver (I), strontium, iron (II), copper (I), yttrium and cadmium.

In one aspect of the invention, the process comprises the steps of forming a solvent system comprising of 5-sulfoisophthalic acid; a metal cation producing compound; and acetic acid, water, or mixtures of acetic acid and water. For example, the solvent system may comprise only water or only acetic acid. Alternatively, the solvent system may comprise a mixture of both acetic acid and water.

Using more numerical terms to describe the solvent system, one could describe the solvent system as comprising acetic acid and water wherein the acetic acid to water ratio is between and includes 1:0 and 0:1. Other solvents or liquids may be present in the solvent system to the extent they do not hinder the reaction that produces MtSIPA or otherwise adulterate the process or final product.

The method of forming the solvent system may vary depending upon the needs of the particular manufacturing process. For example, one may create a solution of HSIPA and a separate solution of the metal cation producing compound then combine the two. One may add a solid metal cation producing compound to a solution of HSIPA. One may add solid HSIPA to a solution of a metal cation producing compound. It is understood that in each instance the term solution includes acetic acid and/or water in the ratios described above.

The time required to combine the components can vary substantially based upon need and preference. For example, the use of a solid metal cation producing compound may require a longer time to combine the components due to material handling constraints. Combining two solutions could occur relatively quickly given the proper piping and pumps. In most instances it is envisioned that initiating contact between the HSIPA and the metal cation producing compound will occur over a period of a few minutes to an hour to ensure proper molar ratios, to improve safety, and to make any pH adjustments that might be necessary.

The stoichiometry between the metal cation and the HSIPA can vary to some extent. Typically the mole ratio of metal cation to HSIPA is around 1:1 for optimum yield. In preferred embodiments the ratio can vary from 0.75:1 to 1.25:1, more preferably from 0.85:1 to 1.15:1, and most preferably from about 0.95:1 to 1.05:1 with cost being a primary consideration in determining the ultimate ratio. However, in general, it is preferable if the metal cation is kept as the limiting reagent with the metal to HSIPA ratio maintained between 0.95:1 to 1:1.

Similarly, the quantity of the solvent system and the ratios of the various components of the solvent system can vary depending on the requirements of the particular manufacturing process. As noted above, the relative amounts of water and acetic acid utilized in the solvent system can range from 100% water to 100% acetic acid to a combination in between. As will be discussed in more detail below, processes that utilize high levels of water in the solvent system will likely employ filtrate recycle to obtain improved yields.

In most instances, the reaction that occurs by contacting the metal cation producing compound with the HSIPA in the solvent system is considered to be virtually instantaneous for those metal compounds that are immediately soluble or are added in a dissolved state. Typically a slurry of solid product (MtSIPA) forms almost immediately in the solvent system. The ratio of solids to total solvent (water; acetic acid; or water plus acetic acid for solvent systems that use both) can vary from about 5% solids by weight to more than 50% solids by weight depending upon the relative amounts of HSIPA and metal compounds to the liquid components of the solvent system. Those skilled in the art are capable of optimizing the solid to liquid ratio to best fit their manufacturing conditions. A percent of solids that works well in many processes appears to be around 25%. This percentage is reduced even further in one alternative embodiment of the process according to the invention discussed below.

Once the product slurry forms, one may cool the solvent system (typically to around 25° C.) to crystallize any MtSIPA that is in solution. The crystallized product is then filtered to recover the MtSIPA product.

However, in some industrial processes, particularly those using expensive metals, additional heating and crystallization steps can be utilized to improve the quality of the product. In these processes, after mixture of the components, the solvent system and its components are heated to drive some or all of the product slurry into solution. The product slurry is heated because it is thought that in some instances the resulting product slurry may be amorphous with trace impurities occluded in the product particles. Heating the mixture to drive most or all of the product particles into solution followed by cooling to allow slow crystallization of the dissolved MtSIPA usually generates product crystals where most if not all of the impurities are excluded. Filtering the overall mixture while the product is in solution is an additional step that can be utilized to remove and reclaim impurities, which may prove valuable depending on the price of the metal utilized. In some cases, depending upon the quality of the reactants, heating slurries that do not fully dissolve may still provide some purification through selective dissolution of impurities in the particle or crystal.

The amount of heat added to the system will vary depending upon the metal compound added to the system (e.g., some silver (I) salts are more soluble than others) and the temperature of the components that form the solvent system. For example, the liquid components of the solvent system can be pre-heated if desired. Samples run using silver (I) salts indicate that heating the charged solvent system to a temperature between about 100° C. and about 120° C. is sufficient to achieve an acceptable quality Ag(I)SIPA product as discussed above. Heating to reflux can be utilized as well. Those skilled in the art will know how to adjust temperature conditions to best fit their particular components and manufacturing equipment.

The charged solvent system is held at reaction conditions for a time sufficient to achieve maximum conversion of reactants (e.g., dissolving metal salts that need heat to fully enter solution) and to achieve acceptable quality. In most instances the "hold time" for the reaction can range from just the time needed to charge the system to an hour or more. In most instances it is envisioned that the hold time will be for a period of between about 10 minutes and 1 hour. Practitioners should strive to reduce reaction times to improve efficiencies and reduce production costs. Process optimization through use of standard procedures such as sampling are known to those skilled in the art and need not be discussed here.

After the reaction is complete and the desired level of product is in solution (e.g, if heat was maintained or added to drive more of the product slurry into solution), the solvent system is cooled, if needed, to induce crystallization of the dissolved product. Typically, cooling the mixture to about 25° C. will induce crystallization of most MtSIPA products. The resulting slurry is then filtered and preferably washed. In preferred embodiments the wash is conducted with acetic acid, or water, or an acetic acid/water mixture to obtain a wet cake of MtSIPA ranging from approximately 30% to 95% yield based on the metal salt used, the metal cation charge, and the ratio of acetic acid to water used.

The ratio of acetic acid to water in the wash, which can be between and including 1:0 and 0:1, can vary depending on the metal salt used and other production variables. For example, acetic acid is a preferred wash for silver (I) due to the low solubility of AgSIPA in it. Alternative wash solvents are also acceptable depending on solubility of the product, interaction with residual filtrate and ease of evaporation. The wash quantity can vary substantially although a small displacement wash is advantageous.

The wet product can be dried to remove water and acetic acid or other wash material. Normal methods of drying are utilized. Depending upon the wash used and the metal, the end product is typically an anhydrous solid or a solvate. Those skilled in the art can change the wash characteristics and/or drying conditions to meet their needs regarding anhydrous vs. solvate products. The final product is then packaged and sold. Thus, the invention also encompasses the metal salts (and compositions of matter comprising those metal salts) prepared according the processes described herein in which the metal cation is selected from the group consisting of silver (I), sodium, potassium, rubidium, cesium, magnesium, calcium, strontium, barium, manganese (II), iron (II), cobalt (II), nickel (II), copper (I), copper (II), zinc, yttrium, and cadmium.

A variation of the above process incorporates a filtrate recycle. This variation can result in a product that has less undesired insoluble compounds while increasing the overall yield of the process. In this variation the quantity of solvent utilized is that which is sufficient to fully dissolve the MtSIPA product under the application of heat as described above. Typically this involves reducing the percent solids in the solvent system to less than about 11% by weight. For example, 77 g of HSIPA (dry basis) and 33 g of silver oxide would likely require approximately 832 g of 67/33 acetic acid and water solvent to fully dissolve the resulting product. Alternatively, since Ag(I)SIPA is more soluble in water than in acetic acid, one could increase the amount of water in the solvent system or use only water. Similar calculations and adjustments for other metals are within the knowledge of those skilled in the art.

As with processes that do not use recycle, the solvent system can be filtered prior to inducing crystallization to remove insoluble impurities. After removing insoluble impurities, crystallization of MtSIPA is induced by cooling followed by recovery of product (typically by filtering) and a wash.

Filtrate recycle is effective at increasing the yield of some MtSIPA such as Ag(I)SIPA which require expensive metal salts. For example, when making Ag(I)SIPA and water is the sole solvent and wash material, recycle of the filtrate and wash for reuse in subsequent batches as part of the solvent system has been shown to increase the yield from approximately 30% for a first batch (fresh water charge) to approximately 100% for second and subsequent batches. Excluding the first batch, which may contain significant insoluble metal content depending on the metal, the quality of the MtSIPA for the second and subsequent batches is generally quite good. The insoluble elemental and metal salts isolated during the clarification step can be reclaimed and reused using methods commonly known in the industry to further increase the yield based on the metal.

As discussed above, the claimed invention also encompasses various metal salts of HSIPA. More specifically, the claimed invention includes a composition of matter comprising the reaction product of 5-sulfoisophthalic acid and a metal cation producing compound wherein the metal cation is selected from the group consisting of silver (I), strontium, iron (II), copper (I), yttrium, and cadmium. The various metal cation producing compounds (e.g., metal salts) utilized in this embodiment of the invention are the same as those utilized in the process according to the invention.

In another aspect, the claimed composition of matter comprises the reaction product of HSIPA, preferably a high quality HSIPA (e.g., one that has been previously isolated from a sulfonation solution and washed to remove sulfuric acid), and a metal cation producing compound where both are reacted in a solvent system as described above. The resulting reaction product can be recovered and dried as discussed above to provide a high quality metal salt of HSIPA.

In another aspect, the invention comprises a metal salt of 5-sulfoisophthalic acid wherein the metal cation is selected from the group consisting of silver (I), strontium, iron (II), copper (I), yttrium, and cadmium. In yet another aspect, the invention comprises each of the above mentioned salts individually. Thus the invention comprises Ag(I)SIPA. The invention comprises $Sr(SIPA)_2$. The invention comprises $Fe(SIPA)_2$. The invention comprises Cu(I)SIPA. The invention comprises $Y(SIPA)_3$. The invention comprises $Cd(SIPA)_2$.

In yet another aspect, the invention comprises a composition of matter comprising a metal salt of 5-sulfoisophthalic acid, including but not limited to each of the following salts, either alone or in combination with each other: Ag(I)SIPA, $Sr(SIPA)_2$, $Fe(SIPA)_2$, Cu(I)SIPA, $Y(SIPA)_3$, and $Cd(SIPA)_2$.

The following examples are provided for purposes of illustration and should not be interpreted as limiting the scope of the invention, which is defined by the claims. For example, not every possible variation of acetic acid and water percentages are shown. Those skilled in the art can determine the solvent system that best fits their production equipment without undue experimentation.

Please note that the total reported percentages in the examples (weight percent SIPA+% Mt+% sulfate+% acetate+% water=total) may not equal 100% due to test method variability. In addition to the quantitative numbers presented below, the presence of the MtSIPA salts was confirmed qualitatively in many instances. For example, when making the silver (I) salt, the presence of AgSIPA was confirmed by the disappearance of silver (I) salt in the reactions (e.g., the disappearance of dark colored silver oxide) and the formation the white/off-white product crystals.

EXAMPLES

The examples begin in the same manner as the detailed description—with the sulfonation of isophthalic acid to form HSIPA.

Sulfonation of Isophthalic Acid

1. Set up a 1000 mL Round-bottom flask.
2. Add 400 g of 30% oleum.
3. While keeping the temperature below 80° C., slowly add 207.7 g of isophthalic acid.
4. Heat the batch to 200 to 205° C.
5. Hold at 200 to 205° C. for 6 hours.
6. Set up a second 100 mL flask. And add 268 g of deionized water.
7. Cool the contents of the second flask (water) to 0 to 5° C.
8. Cool the contents of the first flask (sulfonation mixture) to 160 to 165° C.
9. Slowly drown the contents of the first flask into the second flask at <110° C.
10. Cool the contents of the second flask to 25 to 30° C. to precipitate HSIPA.
11. Filter on a sintered glass funnel and wash twice with 113.5 g of acetic acid.
12. Dry in a vacuum oven.

Example 1

AgSIPA Preparation Using Silver Acetate in Acetic Acid/Water

The steps for preparing AgSIPA using silver acetate as the silver (I) cation producing compound are as follows. Set up a 1000 mL round-bottom flask. Add 240 grams of acetic acid. Add 26.2 g of deionized water. Add 48.4 grams of AgOAc (silver acetate). Add 79.6 grams of HSIPA (Assay: 94.2%; Water: 4.8%; $H_2SO_4$: 0.32%; Iron: 0.35 ppm). Heat the slurry to reflux (around 113° C.) and hold for 30 minutes (note: the hold time is not particularly critical). Cool to around 25° C. Filter and pull vacuum to remove the filtrate. Wash twice with 30 g of acetic acid. Pull the wash through with vacuum. Dry in vacuum oven at 100 to 110° C.

The resulting material assayed as follows:

| | |
|---|---|
| Weight, grams | 112.8 |
| LC Wt % SIPA | 66.3 |
| Ag, % Gravimetric | 27.14 |
| Sulfate, % as $SO_4$ | 0.15 |
| Acetate, % as OAc | 1.94 |
| Water, % KF | 5.11 |
| Yield, % Dry Basis | 94.2 |

Example 2

AgSIPA Preparation Using Silver Oxide in Acetic Acid/Water

HSIPA prepared in accordance with the sulfonation steps described above was utilized in the practice of this Example. The steps for preparing AgSIPA using silver oxide as the silver (I) cation producing compound are as follows. Set up a 1000 mL round-bottom flask. Add 270 grams of acetic acid. Add 30 g of deionized water (DI). Add 33 grams of $Ag_2O$ (silver oxide). Add 78.9 grams of HSIPA (Assay: 97.6%; Water: 3.2%; $H_2SO_4$: 1.16%). Heat the slurry to reflux (around 110 to 120° C.). Cool to around 25° C. Filter and pull vacuum to remove the filtrate. Wash twice with 50 g of acetic acid. Pull the wash through with vacuum. Dry in vacuum oven at 100 to 110° C.

The resulting material assayed as follows:

| | |
|---|---|
| Weight, grams | 103.0 |
| LC Wt % SIPA | 65.3 |
| Ag, % (Gravimetric) | 26.56 |
| Sulfate, % as $SO_4$ | 0.66 |
| Acetate, % as OAc | 2.92 |
| Water, % KF | 0.37 |
| Yield, % dry basis | 99.1 |

Example 3

AgSIPA Preparation Using Silver Oxide in Water with Filtrate Recycle

HSIPA prepared as above was utilized in the practice of this Example. The steps for preparing AgSIPA using silver oxide in water with a filtrate recycle are as follows. Set up a 1000 mL round-bottom flask. Add 200 g of deionized water (first batch only) or the filtrate from the prior batch (second and subsequent batches) plus fresh make-up water up to 200 g. Add 33 grams of $Ag_2O$ (silver oxide). Add 81.7 grams of HSIPA (Assay: 94.2%; Water: 5.37%; $H_2SO_4$: 0.03%; Iron: 6 ppm). Heat the solution to 100° C. At 100 to 105° C. filter the batch through 1.2 micron glass-fiber filter paper to remove Ag and insoluble Ag salts. Reheat the filtrate to 100° C. then cool to around 25° C. to recrystallize Ag(I)SIPA product. Filter the product and pull vacuum to remove the filtrate. Wash twice with 15 g of 0 to 5° C. water. Pull the wash through with vacuum. Dry in vacuum oven at 100 to 110° C. Repeat the process with filtrate from the prior batches.

The resulting materials assayed as follows.

| | Batch 1 | Batch 2 | Batch 3 | Batch 4 |
|---|---|---|---|---|
| Product Weight, grams | 31.2 | 103.0 | 103.7 | 104.0 |
| LC Wt % SIPA | 58.7 | 75.9 | 74.8 | 73.1 |
| Ag, % (gravimetric) | 44.7 | 29.1 | 29.0 | 29.3 |
| Sulfate, ppm as $SO_4$ | <100 | <100 | 166 | 275 |
| Acetate, ppm as OAc | <100 | <100 | <100 | <100 |
| Water, % KF | 0.44 | 0.31 | 0.46 | 2.35 |
| Yield, % Dry Basis | 30.9 | 103.3 | 102.7 | 101.1 |

Example 4

NaSIPA in Water

To a 1000 mL round-bottom flask is added 280.8 grams of DI water, 93.7 g of Sodium Hydroxide (50% in water) and 320.2 g of HSIPA (93.7% Assay; 6.0% Water; and 0.06% Strong Acid as $H_2SO_4$). The batch is heated to reflux (106.8° C.), cooled to 55° C., held one half hour then cooled to 15° C. The slurry is filtered on a sintered glass funnel and washed with 75 g of DI water (0 to 5° C.). The product is dried in a 110 to 120° C. vacuum oven to give 187.9 grams of white solid. NOTE: With filtrate recycle, the yield stabilized around 89% with comparable quality.

The product assayed as follows:

| | |
|---|---|
| Weight, grams | 187.9 |
| NaSIPA Assay, % | 99.62 |
| Sulfate, ppm as $SO_4$ | <100 |
| Acidity, % as $H_2SO_4$ | 0 |
| Water, % KF | 0.13 |
| Yield, % Assay Basis | 57.3 |

Example 5

NaSIPA in Acetic Acid/Water

To a 2000 mL round-bottom flask is added 691.5 grams of acetic acid, 83.5 g of DI water, 72.91 g of sodium hydroxide (50% in water) and 250 g of HSIPA (94.4% Assay; 4.4% Water; and 0.85% Strong Acid as $H_2SO_4$). The batch is heated to reflux (106.3° C.) cooled to 25° C. and held for one hour. The slurry is filtered on a sintered glass funnel and washed with 2×63 g of acetic acid. The product is dried in a 160 to 165° C. vacuum oven to give 244.7 grams of off-white solid. NOTE: Water-wet acetic acid can be recovered by distillation and recycled to subsequent batches to provide product with comparable quality and yield.

The product assayed as follows:

| | |
|---|---|
| Weight, grams | 244.7 |
| NaSIPA Assay, % | 100.7 |
| Sulfate, ppm as $SO_4$ | <100 |
| Acetate, ppm as OAc | 6886 |
| Acidity, % as $H_2SO_4$ | 0 |
| Water, % KF | 0.24 |
| Yield, % Assay Basis | 95.2 |

Example 6

KSIPA in Water

To a 1000 mL round-bottom flask is added 92.5 grams of DI water, 48.55 g of KOH (45% in water) and 108.0 g of HSIPA (92.6% Assay; 6.95% Water; and 0.07% Strong Acid as $H_2SO_4$). The batch is heated to reflux (105.2° C.), cooled to 55° C., held one half hour then cooled to 15° C. The slurry is filtered on a sintered glass funnel and washed with 0 to 5° C. DI water (25 g). The product is dried in a 110 to 120° C. vacuum oven to give 107.8 grams of white solid. NOTE: With filtrate recycle, the yield stabilizes around 96% with comparable quality.

The product assayed as follows:

| | |
|---|---|
| Weight, grams | 107.8 |
| KSIPA Assay, % | 99.64 |
| Sulfate, ppm as $SO_4$ | <100 |
| Acetate, ppm as OAc | 0 |
| Acidity, % as $H_2SO^4$ | 0.04 |
| Water, % KF 0.84 | 0.84 |
| Yield, % Assay Basis | 93.0 |

Example 7

KSIPA in Acetic Acid/Water

To a 1000 mL round-bottom flask is added 250 grams of acetic acid, 10 g of DI water, 16.0 g of potassium hydroxide pellets and 78.7 g of HSIPA (95.3% Assay; 4.3% Water; and 0.9% Strong Acid as $H_2SO_4$). The batch is heated to reflux, held one hour and cooled to 25° C. over 2 hours. The slurry is filtered on a sintered glass funnel and washed with 35 g of acetic acid. The product is dried in a 140° C. vacuum oven to give 68.8 grams of white solid.

The product assayed as follows:

| | |
|---|---|
| Weight, grams | 68.8 |
| KSIPA Assay, % | 100.3 |
| Sulfate, ppm as $SO_4$ | <100 |
| Acetate, ppm as OAc | 215 |
| Acidity, % as H2504 | 0 |
| Water, % KF 0.16 | 0.16 |
| Yield, % Assay Basis | 79.4 |

Example 8

RbSIPA in Acetic Acid/Water

To a 1000 mL round-bottom flask is added 240 grams of acetic acid, 27.6 g of DI water, 59.4 g of rubidium hydroxide (50% in water) and 77.9 g of HSIPA (96.3% Assay; 3.11% Water; and 0.05% Strong Acid as $H_2SO_4$). The batch is heated to reflux (110.8° C.), held 30 minutes, cooled to 25° C. and held one hour. The slurry is filtered on a sintered glass funnel and washed with 2×30 g of acetic acid. The product is dried in a 100 to 110° C. vacuum oven to give 85.6 grams of white solid.

The product assayed as follows:

| | |
|---|---|
| Weight, grams | 85.6 |
| SIPA Moiety, LC | Confirmed |
| Rb, X-ray fluorescence | Confirmed |
| Sulfate, ppm as $SO_4$ | 432 |
| Acetate, ppm as OAc | 413 |
| Acidity, % as $H_2SO_4$ | 0 |
| Water, % KF | 0.11 |
| Yield, % Dry Basis | 84.9 |

Example 9

CsSIPA in Acetic Acid/Water

To a 1000 mL round-bottom flask is added 240 grams of acetic acid, 46.6 g of DI water, 48.63 g of cesium hydroxide monohydrate and 78.8 g of HSIPA (95.2% Assay; 4.66% Water; and 0.06% Strong Acid as $H_2SO_4$). The batch is heated to reflux (115° C.), held 30 minutes, cooled to 25° C. and held one hour. The slurry is filtered on a sintered glass funnel and washed with 2×30 g of acetic acid. The product is dried in a 110 to 120° C. vacuum oven to give 58.3 grams of white solid.

The product assayed as follows:

| | |
|---|---|
| Weight, grams | 58.3 |
| SIPA Moiety, LC | Confirmed |
| Cs, X-ray fluorescence | Confirmed |
| Sulfate, ppm as $SO_4$ | <100 |
| Acetate, ppm as OAc | 650 |
| Acidity, % as $H_2SO_4$ | 0 |
| Water, % KF | 0.29 |
| Yield, % Dry Basis | 50.6 |

Example 10

$Mg(SIPA)_2$ in Water

To a 1000 mL round-bottom flask is added 100 g of DI water, 8.46 g of magnesium hydroxide and 75 g of HSIPA (0.305 mol). The batch is heated to reflux and 32 mL of water are removed by distillation. The batch is cooled to 25° C. and held overnight. The slurry is filtered on a sintered glass funnel and no wash is applied. The product is dried in a 140 to 155° C. vacuum oven to give 44.4 grams of white solid.

The product assayed as follows:

| | |
|---|---|
| Weight, grams | 44.4 |
| SIPA Moiety, LC | Confirmed |
| Mg, X-ray fluorescence | Confirmed |
| Sulfate, ppm as $SO_4$ | 8583 |
| Acetate, ppm as OAc | 260 |
| Acidity, % as $H_2SO_4$ | 1.08 |
| Water, % KF | 4.85 |
| Yield, % Calc Assay Basis | 52.9 |

Example 11

$Mg(SIPA)_2$ in Acetic Acid/Water

To a 1000 mL round-bottom flask is added 450 grams of acetic acid, 50 g of DI water, 8.46 g of magnesium hydroxide and 79.6 g of HSIPA (94.3% Assay; 4.97% Water; and 0.11% Strong Acid as $H_2SO_4$). The batch is heated to reflux, held one hour and cooled to 25° C. The slurry is filtered on a sintered glass funnel and washed with 2×35 g of acetic acid. The product is dried in a 140° C. vacuum oven to give 72.5 grams of white solid.

The product assayed as follows:

| | |
|---|---|
| Weight, grams | 72.5 |
| SIPA Moiety, LC | Confirmed |
| Mg, X-ray fluorescence | Confirmed |
| Sulfate, ppm as SO | <100 |
| Acetate, ppm as OAc | 947 |
| Acidity, % as $H_2SO_4$ | 0 |
| Water, % KF | 10.6 |
| Yield, % Calc Assay Basis | 82.5 |

Example 12

$Ca(SIPA)_2$ in Acetic Acid/Water

To a 1000 mL round-bottom flask is added 400 grams of acetic acid, 25 g of DI water, 25.5 g of calcium acetate hydrate and 79.6 g of HSIPA (94.28% Assay; 4.97% Water; and 0.11% Strong Acid as $H_2SO_4$). The batch is heated to reflux (112° C.), held one hour and cooled to 25° C. The slurry is filtered on a sintered glass funnel and washed with 2×35 g of acetic acid. The product is dried in a 150 to 155° C. vacuum oven to give 78.1 grams of white solid.

The product assayed as follows:

| | |
|---|---|
| Weight, grams | 78.1 |
| SIPA Moiety, LC | Confirmed |
| Ca, X-ray fluorescence | Confirmed |
| Sulfate, ppm as $SO_4$ | 581 |
| Acetate, ppm as OAc | 15098 |

-continued

| | |
|---|---|
| Acidity, % as H$_2$SO$_4$ | 0 |
| Water, % KF | 1.2 |
| Yield, % Calc Assay Basis | 93.9 |

Example 13

Sr(SIPA)$_2$ in Water

To a 1000 mL round-bottom flask is added 150 g of DI water, 27.5 g of strontium hydroxide octahydrate and 50 g of HSIPA (94.0% Assay; 5.2% Water; and 1073 ppm sulfate). The batch is heated to 100° C. and cooled to 25° C. The slurry is filtered on a sintered glass funnel and 16 grams of cold DI water wash at 5 to 10° C. is applied. The product is dried in a 100° C. vacuum oven to give 39.8 grams of white solid.

The product assayed as follows:

| | |
|---|---|
| Weight, grams | 39.8 |
| SIPA Moiety, LC | Confirmed |
| Sr, X-Ray Fluorescence | Confirmed |
| Sulfate, ppm as SO$_4$ | 1615 |
| Acetate, ppm as OAc | 0 |
| Acidity, % as H$_2$SO$_4$ | 0 |
| Water, % KF | 0.34 |
| Yield, % Calc Assay Basis | 71.5 |

Example 14

Sr(SIPA)$_2$ in Acetic Acid/Water

To a 1000 mL round-bottom flask is added 300 grams of acetic acid, 20 g of DI water, 41.7 g of strontium hydroxide octahydrate and 77.3 g of HSIPA (97% Assay; 2.8% Water; and 4424 ppm sulfate). The batch is heated to 100° C. and cooled to 25° C. The slurry is filtered on a sintered glass funnel and washed with 30 g of acetic acid. The product is dried in a 100° C. vacuum oven to give 79.4 grams of white solid.

The product assayed as follows:

| | |
|---|---|
| Weight, grams | 79.4 |
| SIPA Moiety, LC | Confirmed |
| Sr, X-Ray Fluorescence | Confirmed |
| Sulfate, ppm as SO$_4$ | 2695 |
| Acetate, ppm as OAc | 31060 |
| Acidity, % as H$_2$SO$_4$ | 0 |
| Water, % KF | 0.9 |
| Yield, % Calc Assay Basis | 86.1 |

Example 15

Ba(SIPA)$_2$ in Acetic Acid/Water

To a 1000 mL round-bottom flask is added 400 grams of acetic acid, 100 g of DI water, 24.8 g of barium hydroxide and 78.8 g of HSIPA (94.3% Assay; 4.97% Water; and 0.11% Strong Acid as H$_2$SO$_4$). The batch is heated to reflux, held one hour and cooled to 25° C. The slurry is filtered on a sintered glass funnel and washed with 2×35 g of acetic acid. The product is dried in a 140 to 155° C. vacuum oven to give 84.0 grams of white solid.

The product assayed as follows:

| | |
|---|---|
| Weight, grams | 84 |
| SIPA Moiety, LC | Confirmed |
| Ba, X-Ray Fluorescence | Confirmed |
| Sulfate, ppm as SO$_4$ | 585 |
| Acetate, ppm as OAc | 13993 |
| Acidity, % as H$_2$SO$_4$ | 0 |
| Water, % KF | 1.48 |
| Yield, % Calc Assay Basis | 86.1 |

Example 16

Mn(SIPA)$_2$ in Acetic Acid/Water

To a 1000 mL round-bottom flask is added 450 grams of acetic acid, 47.8 g of DI water, 35.5 g of manganese acetate tetrahydrate and 77.9 g of HSIPA (96.3% Assay; 3.11% Water; and 0.05% Strong Acid as H$_2$SO$_4$). The batch is heated to reflux, held 30 minutes and cooled to 25° C. The slurry is filtered on a sintered glass funnel and washed with 2×30 g of acetic acid. The product is dried in a 150° C. vacuum oven to give 90.4 grams of white solid.

The product assayed as follows:

| | |
|---|---|
| Weight, grams | 90.4 |
| SIPA Moiety, LC | Confirmed |
| Mn, X-Ray Fluorescence | Confirmed |
| Sulfate, ppm as SO$_4$ | 124 |
| Acetate, ppm as OAc | 43884 |
| Acidity, % as H$_2$SO$_4$ | 0 |
| Water, % KF | 6.27 |
| Yield, % Calc Assay Basis | 97.2 |

Example 17

Fe(SIPA)$_2$ in Water

To a 1000 mL round-bottom flask is added 90 g of DI water, 58.7 g of iron sulfate heptahydrate and 102.6 g of HSIPA (98.3% Assay; 1.6% Water; and 4158 ppm sulfate). The batch is heated to 90° C. and cooled to 25° C. The slurry is filtered on a sintered glass funnel and 30 grams of cold DI water wash is applied. The product is dried in a 100° C. vacuum oven to give 42.4 grams of a light green solid.

The product assayed as follows:

| | |
|---|---|
| Weight, grams | 42.4 |
| SIPA Moiety, LC | Confirmed |
| Fe, X-Ray Fluorescence | Confirmed |
| Sulfate, ppm as SO$_4$ | 3989 |
| Acetate, ppm as OAc | <100 |
| Acidity, % as H$_2$SO$_4$ | 0.69 |
| Water, % KF | 10.98 |
| Yield, % Calc Assay Basis | 33.5 |

Example 18

Co(SIPA)$_2$ in Acetic Acid/Water

To a 1000 mL round-bottom flask is added 450 grams of acetic acid, 20 g of DI water, 36.1 g of cobalt acetate tetrahydrate and 80.6 g of HSIPA (92.7% Assay; 6.8% Water; and 0.19% Strong Acid as H$_2$SO$_4$). The batch is heated to reflux (111.5° C.), held one hour and cooled to 25° C. The slurry is filtered on a sintered glass funnel and washed with 35 g of acetic acid. The product is dried in a 140° C. vacuum oven to give 94.4 grams of light pink solid.

The product assayed as follows:

| Weight, grams | 94.4 |
| SIPA Moiety, LC | Confirmed |
| Co, X-Ray Fluorescence | Confirmed |
| Sulfate, ppm as $SO_4$ | 813 |
| Acetate, ppm as OAc | 47619 |
| Acidity, % as $H_2SO_4$ | 0.04 |
| Water, % KF | 10.89 |
| Yield, % Calc Assay Basis | 95.4 |

Example 19

$Ni(SIPA)_2$ in Acetic Acid/Water

To a 1000 mL round-bottom flask is added 450 grams of acetic acid, 20 g of DI water, 36.1 g of nickel acetate tetrahydrate and 80.6 g of HSIPA (92.7% Assay; 6.8% Water; and 0.19% Strong Acid as $H_2SO_4$). The batch is heated to reflux (111° C.), held one hour and cooled to 25° C. The slurry is filtered on a sintered glass funnel and washed with 35 g of acetic acid. The product is dried in a 140° C. vacuum oven to give 97.8 grams of light green solid.

The product assayed as follows:

| Weight, grams | 97.8 |
| SIPA Moiety, LC | Confirmed |
| Ni, X-Ray Fluorescence | Confirmed |
| Sulfate, ppm as $SO_4$ | 291 |
| Acetate, % as OAc | 20176 |
| Acidity, % as $H_2SO_4$ | 0.02 |
| Water, % KF | 11.26 |
| Yield, % Calc Assay Basis | 101.8 |

Example 20

$Cu(SIPA)_2$ in Acetic Acid/Water

To a 1000 mL round-bottom flask is added 350 grams of acetic acid, 20 g of DI water, 28.9 g of copper (II) acetate hydrate and 81.3 g of HSIPA (92.7% Assay; 6.8% Water; and 0.19% Strong Acid as $H_2SO_4$). The batch is heated to reflux and cooled to 25° C. The slurry is filtered on a sintered glass funnel and washed with 35 g of acetic acid. The product is dried in a 140 to 155° C. vacuum oven to give 83.6 grams of light blue solid.

The product assayed as follows:

| Weight, grams | 83.6 |
| SIPA Moiety, LC | Confirmed |
| Cu, X-Ray Fluorescence | Confirmed |
| Sulfate, ppm as $SO_4$ | 8089 |
| Acetate, ppm as OAc | 7985 |
| Acidity, % as $H_2SO_4$ | 1.62 |
| Water, % KF | 1.18 |
| Yield, % Calc Assay Basis | 95.8 |

Example 21

CuSIPA in Acetic Acid/Water

To a 1000 mL round-bottom flask is added 300 grams of acetic acid, 20 g of DI water, 22.5 g of copper (I) oxide and 78.9 g (95% Assay; 4.3% Water; and 4839 ppm Sulfate) of HSIPA. The batch is heated to 100° C. cooled to 25° C. The slurry is filtered on a sintered glass funnel and washed with 30 g of acetic acid. The product is dried in a 100° C. vacuum oven to give 104.1 grams of light purple solid.

The product assayed as follows:

| Weight, grams | 104.1 |
| SIPA Moiety, LC | Confirmed |
| Cu, X-Ray Fluorescence | Confirmed |
| Sulfate, ppm as SO4 | 2683 |
| Acetate, ppm as OAc | 2534 |
| Acidity, % as H2SO4 | 0 |
| Water, % KF | 8.3 |
| Yield, % Calc Assay Basis | 101.0 |

Example 22

$Zn(SIPA)_2$ in Acetic Acid/Water

To a 1000 mL round-bottom flask is added 350 grams of acetic acid, 40 g of DI water, 33.5 grams of zinc acetate dihydrate and 77.1 g (97.2% Assay; 2.6% Water; and 4546 ppm Sulfate) of HSIPA. The batch is heated to 95° C. cooled to 25° C. The slurry is filtered on a sintered glass funnel and washed with 2×30 g of acetic acid. The product is dried in a 100° C. vacuum oven to give 86.9 grams of a white solid.

The product assayed as follows:

| Weight, grams | 86.9 |
| SIPA Moiety, LC | Confirmed |
| Zn, X-Ray Fluorescence | Confirmed |
| Sulfate, ppm as $SO_4$ | 1480 |
| Acetate, ppm as OAc | 2379 |
| Acidity, % as $H_2SO_4$ | |
| Water, % KF | 8.97 |
| Yield, % Calc Assay Basis | 73.0 |

Example 23

$Y(SIPA)_3$ in Acetic Acid/Water

To a 1000 mL round-bottom flask is added 300 grams of acetic acid, 20 g of DI water, 30.1 g of yttrium acetate hydrate and 78.9 g (95% Assay; 4.3% Water; and 4839 ppm Sulfate) of HSIPA. The batch is heated to 100° C. cooled to 25° C. The slurry is filtered on a sintered glass funnel and washed with 2×30 g of acetic acid. The product is dried in a 100° C. vacuum oven to give 63.0 grams of a white solid.

The product assayed as follows:

| Weight, grams | 63.0 |
| SIPA Moiety, LC | Confirmed |
| Y, X-Ray Fluorescence | Confirmed |
| Sulfate, ppm as $SO_4$ | 1950 |
| Acetate, ppm as OAc | 21311 |
| Acidity, % as $H_2SO_4$ | 0 |
| Water, % KF | 0.7 |
| Yield, % Calc Assay Basis | 73.0 |

Example 24

Cd(SIPA)₂ in Water

To a 1000 mL round-bottom flask is added 133 g of DI water, 41.8 g of cadmium acetate dihydrate and 77.1 g (97.2% Assay; 2.6% Water; and 4546 ppm Sulfate) of HSIPA. The batch is heated to 100° C. cooled to 25° C. The slurry is filtered on a sintered glass funnel and washed with 10 g of 0 to 5° C. DI water. The product is dried in a 100 to 130° C. vacuum oven to give 34.6 grams of a white solid.

The product assayed as follows:

| Weight, grams | 34.6 |
|---|---|
| SIPA Moiety, LC | Confirmed |
| Cd, X-Ray Fluorescence | Confirmed |
| Sulfate, ppm as $SO_4$ | 173 |
| Acetate, ppm as OAc | 677 |
| Acidity, % as $H_2SO_4$ | 0 |
| Water, % KF | 6.78 |
| Yield, % Calc Assay Basis | 35.1 |

Example 25

Cd(SIPA)₂ in Acetic Acid/Water

To a 1000 mL round-bottom flask is added 40 g of DI water, 300 g of acetic acid, 41.8 of cadmium acetate dihydrate and 77.1 g (97.2% Assay; 2.6% Water; and 4546 ppm Sulfate) of HSIPA. The batch is heated to 100° C. cooled to 25° C. The slurry is filtered on a sintered glass funnel and washed with 30 g of acetic acid. The product is dried in a 100 to 130° C. vacuum oven to give 82.8 grams of a white solid.

The product assayed as follows:

| Weight, grams | 82.8 |
|---|---|
| SIPA Moiety, LC | Confirmed |
| Cd, X-Ray Fluorescence | Confirmed |
| Sulfate, ppm as $SO_4$ | 1190 |
| Acetate, ppm as OAc | 43208 |
| Acidity, % as $H_2SO_4$ | 0 |
| Water, % KF | 1.33 |
| Yield, % Calc Assay Basis | 85.0 |

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

That which is claimed is:

1. A process for the preparation of metal salts of 5-sulfoisophthalic acid, the process comprising the steps of:
   forming a solvent system comprising 5-sulfoisophthalic acid, a metal cation producing compound, and acetic acid and water wherein the acetic acid to water ratio is between and includes 0:1 and 1:0 and wherein said metal cation is selected from the group consisting of silver (I), sodium, potassium, rubidium, cesium, magnesium, calcium, strontium, barium, manganese (II), iron (II), cobalt (II), nickel (II), copper (I), copper (II), zinc, yttrium, and cadmium; and
   maintaining said solvent system under conditions sufficient to form a metal salt of 5-sulfoisophthalic acid.

2. A process according to claim 1 wherein said solvent system comprises acetic acid and water.

3. A process according to claim 1 wherein said metal cation producing compound comprises a metal salt.

4. A process according to claim 1 further comprising the prior step of isolating 5-sulfoisophthalic acid from a sulfonation solution and washing said 5-sulfoisophthalic acid prior to forming said solvent system.

5. A process according to claim 1 further comprising the steps of recovery of said metal salt of 5-sulfoisophthalic acid and recycle of said solvent system.

6. A process according to claim 1 wherein said metal cation is selected from the group consisting of sodium, potassium, and rubidium.

7. A process according to claim 1 wherein said metal cation is cesium.

8. A process according to claim 1 wherein said metal cation is selected from the group consisting of magnesium, calcium, and barium.

9. A process according to claim 1 wherein said metal cation is selected from the group consisting of manganese (II), cobalt (II), nickel (II); copper (II), and zinc.

10. A process according to claim 1 wherein said metal cation is selected from the group consisting of silver (I), strontium, iron (II), copper (I), yttrium and cadmium.

11. A process for the preparation of a metal salt of 5-sulfoisophthalic acid, the process comprising the step of contacting previously isolated 5-sulfoisophthalic acid with a metal cation producing compound under conditions sufficient to form a metal salt of 5-sulfoisophthalic acid wherein the metal cation is selected from the group consisting of silver (I), sodium, potassium, rubidium, cesium, magnesium, calcium, strontium, barium, manganese (II), iron (II), cobalt (II), nickel (II), copper (I), copper (II), zinc, yttrium, and cadmium.

12. A process according to claim 11 wherein the step of contacting 5-sulfoisophthalic acid with a metal cation producing compound comprises creating a solvent system comprising said 5-sulfoisophthalic acid; said metal cation producing compound; and acetic acid and water wherein the acetic acid to water ratio is between and includes 0:1 and 1:0 and wherein said metal cation producing compound is a metal salt.

13. A composition of matter comprising the reaction product of 5-sulfoisophthalic acid and a metal cation producing compound wherein the metal cation is selected from the group consisting of silver (I), strontium, iron (II), copper (I), yttrium, and cadmium.

14. A metal salt of 5-sulfoisophthalic acid wherein the metal is selected from the group consisting of silver (I), strontium, iron (II), copper (I), yttrium, and cadmium.

15. A metal salt according to claim 14 wherein the metal is silver (I).

16. A metal salt according to claim 14 wherein the metal is strontium.

17. A metal salt according to claim 14 wherein the metal is iron (II).

18. A metal salt according to claim 14 wherein the metal is copper (I).

19. A metal salt according to claim 14 wherein the metal is yttrium.

20. A metal salt according to claim 14 wherein the metal is cadmium.

21. A composition of matter comprising a metal salt of claim 14.

* * * * *